US00RE38869E

(19) United States
(12) Reissued Patent
Polaschegg et al.

(10) Patent Number: US RE38,869 E
(45) Date of Reissued Patent: Nov. 8, 2005

(54) EXTRACORPOREAL CIRCUIT FOR PERIPHERAL VEIN FLUID REMOVAL

(75) Inventors: Hans-Dietrich Polaschegg, Koestenberg (AT); Steven Bernard, Andover, MN (US); Howard R. Levin, Teaneck, NJ (US); Mark Gelfand, New York, NY (US)

(73) Assignee: CHF Solutions Inc., New York, NY (US)

(21) Appl. No.: 10/936,827

(22) Filed: Sep. 9, 2004

Related U.S. Patent Documents

Reissue of:
(64) Patent No.: 6,533,747
Issued: Mar. 18, 2003
Appl. No.: 09/698,132
Filed: Oct. 30, 2000

U.S. Applications:
(63) Continuation-in-part of application No. 09/660,195, filed on Sep. 12, 2000, now Pat. No. 6,887,214, and a continuation-in-part of application No. 09/618,759, filed on Jul. 18, 2000, now Pat. No. 6,890,315.
(60) Provisional application No. 60/206,232, filed on May 23, 2000.

(51) Int. Cl.[7] ..... A61M 1/34
(52) U.S. Cl. ..... 604/6.09
(58) Field of Search ..... 604/6.09

(56) References Cited

U.S. PATENT DOCUMENTS

| | | | | | |
|---|---|---|---|---|---|
| 4,080,958 | A | * | 3/1978 | Bregman et al. | 600/16 |
| 4,086,924 | A | * | 5/1978 | Latham, Jr. | 604/6.04 |
| 4,599,055 | A | * | 7/1986 | Dykstra | 417/477.2 |
| 4,657,529 | A | * | 4/1987 | Prince et al. | 604/6.11 |
| 4,824,339 | A | * | 4/1989 | Bainbridge et al. | 417/477.2 |
| 4,936,980 | A | * | 6/1990 | Harada et al. | 210/647 |
| 5,114,580 | A | * | 5/1992 | Ahmad et al. | 210/646 |
| 5,312,550 | A | * | 5/1994 | Hester | 210/646 |
| 5,476,451 | A | * | 12/1995 | Ensminger et al. | 604/288.03 |
| 5,536,237 | A | * | 7/1996 | Prince et al. | 604/6.11 |
| 5,685,989 | A | * | 11/1997 | Krivitski et al. | 210/646 |
| 5,707,086 | A | * | 1/1998 | Treu et al. | 285/93 |
| 5,725,776 | A | * | 3/1998 | Kenley et al. | 210/646 |
| 5,762,805 | A | * | 6/1998 | Truitt et al. | 210/645 |
| 5,776,345 | A | * | 7/1998 | Truitt et al. | 210/645 |
| 5,906,589 | A | * | 5/1999 | Gordon et al. | 604/65 |
| 5,910,252 | A | * | 6/1999 | Truitt et al. | 210/645 |
| 6,090,048 | A | * | 7/2000 | Hertz et al. | 600/485 |
| 2002/0068015 | A1 | * | 6/2002 | Polaschegg et al. | 422/44 |

FOREIGN PATENT DOCUMENTS

| | | | |
|---|---|---|---|
| DE | 29 44 062 | * | 9/1976 |
| WO | WO 97/15228 | * | 5/1997 |

OTHER PUBLICATIONS

Pierguiseppe Agostoni et al., "Sustained Improvement in Functional Capacity After Removal of Body Fluid With Isolated Ultrafiltration in Chronic Cardiac Insufficiency (etc.)", Mar. 1994, The American Jounal of Medicine, vol. 96, pp. 191–199.*

(Continued)

*Primary Examiner*—Gerald A. Michalsky
(74) *Attorney, Agent, or Firm*—Nixon & Vanderhye, P.C.

(57) ABSTRACT

An extracorporeal blood circuit is disclosed for withdrawing, filtering and returning blood from peripheral blood vessels. The blood passage in the circuit extends through a withdrawal tube connected to a catheter in a peripheral vein, a filter, one or more pressure sensors and return tube also connected to a catheter in a peripheral vein (which may or may not be the same vein as used for the withdrawal tube). The blood passage is air free, and has smooth passage walls which promoted continuous and uniform flow of the blood through the circuit.

14 Claims, 6 Drawing Sheets

OTHER PUBLICATIONS

Daniel Goldstein et al., "Venoarterial Strunting for the Treatment of Right Sided Circulatory Failure After Left Ventricular Assist Device Placement", ASAIO Journal 1997, pp. 171–176.*

Michael Berkoben et al., "Hemodialysis Vascular Acess", pp. 41–57.*

James Cimino et al.,"Sample Venipuncture For Hemodialysis", The New England Journal of Medicine, Sep. 20, 1962, pp. 608–609.*

Drukker et al., "Replacement of Renal Function Dialysis", pp. 334–379.*

Andrea Rimondini et al., "Hemofiltration as Short–Term Treatment for Refractory Congestive Heart Failure", Jul. 1987, The American Journal of Medicine, vol. 83, pp. 43–48.*

Strife, C.F. et al., "Experience With a Low Volume Ultrafiltration Cell in Small Children", Clincal Nephrology 8:410–413 (1977).*

Lauer, A. et al., "Continuous Arteriovenous Hemofiltration in the Critically Ill Patient, Clinical Use and Operational Characteristics", Annals of Internal Medicine 99:455–460 (1983).*

Verbanck, J. et al., "Pure Ultrafiltration by Repeated Puncture of a Peripheral Arm–Vein as Treatment of Refractory Edema"(Case Report), The International Journal of Artificial Organs, vol. 3, No. 6 (1980) p. 342–343.*

Silverstein et al., "Treatment of Severe Fluid Overload by Ultrafiltration", the New England Jounal of Medicine, vol. 291, No. 15, Oct. 10, 1974, pp. 747–751.*

Blake, P. et al., Refractory Congestive Heart Failure: Overview and Application of Extracorporeal Ultrafiltration, Critical Care Nephrology, Advances in Renal Replacement Therapy, vol. 3, No. 2 (Apr. 1966), pp. 166–173.*

Civati G. et al., "Haemofiltration Without Substitution Fluid", Proc. EDTA–ERA, vol. 21 (1984), pp. 441–446.*

Jenkins, R.D. et al., "The Use of Continuous Arteriovenous Hemofiltration With Hemodialysis in a Newborn", Draft #6, Personal Communication, 1985 (6 pages).*

Jacobs, C. et al., "Continuous Arteriovenous Hemofiltration", Replacement of Renal Function By Dialysis, 4$^{th}$ Ed., (1996) pp. 391–397.*

Gupta, B.B. et al., "High Shear Rate Hemofiltration: Influence of Fiber Dimension and Shear Rates", Artificial Organs, International Society for Artificial Organs, vol. 13(2) (1989), pp. 97–102.*

Donato, L. et al., "Treatment of End–Stage Congestive Heart Failure by Extracorporeal Ultrafiltration", The American Journal of Cardiology, vol. 59, (Feb. 1, 1987), pp. 379–380.*

L'Abbate, A. et al., "Ultrafiltration: A Rational Treatment for Heart Failure", Cardiology 1989, 76:384–390.*

Chen, Y. et al., "Direct Peripheral Venopuncture: Another New Choice of Temporary Vascular Access"(Case Report), Renal Failure, 22(3), 369–377 (2000).*

PRISMA™ M60 Set, "Instructions for Use", pp. 1–6 and 12, (1998).*

* cited by examiner

EXTRACORPOREAL CIRCUIT FOR PERIPHERAL VEIN FLUID REMOVAL

Matter enclosed in heavy brackets [ ] appears in the original patent but forms no part of this reissue specification; matter printed in italics indicates the additions made by reissue.

This application is a continuation-in-part (CIP) application of U.S. patent application Ser. No. 09/618,759, filed Jul. 18, 2000, which is based on Provisional Application 60/206,232, filed May 23, 2000, and a CIP application of U.S. patent application Ser. No. 09/660,195, filed Sep. 12, 2000. These applications are commonly-owned and incorporated by reference in their entirety.

FIELD OF INVENTION

This invention relates to methods and apparatus for treatment of congestive heart failure (CHF) by removal of excessive fluids, such as water. In particular, the invention relates to an extracorporeal circuit with minimized blood residence time.

BACKGROUND OF THE INVENTION

Congestive Heart Failure (CHF) is the only form of heart disease still increasing in frequency. According to the American Heart Association, CHF is the "Disease of the Next Millennium". CHF is a condition that occurs when the heart becomes damaged and reduces blood flow to the organs of the body. If blood flow decreases sufficiently, kidney function becomes impaired and results in fluid retention, abnormal hormone secretion and increased constriction of blood vessels. The fluid overload and associated clinical symptoms resulting from these physiologic changes are the predominant cause for excessive hospital admissions, terrible quality of life and overwhelming costs to the health care system due to CHF.

One possible method for removal of excessive fluid is mechanical fluid removal employing an extracorporeal circuit with a hemofilter. This method is especially useful if CHF is in its final stage and drug treatment is no longer efficient. Extracorporeal fluid removal is a common method used to treat acute renal disease. Fluid removal treatments are usually combined with either hemodialysis or hemofiltration to also remove solutes normally excreted by the kidney. Currently the most advanced device for this treatment is the PRISMA™ system from Gambro, which comprises an air free extracorporeal circuit consisting of a blood tubing system with integrated filter, a plurality of injection or sampling ports and pressure measuring domes. Although attempts have been made to construct a streamlined flow path, the blood flow passage in the PRISMA™ system still had dead zones where fluid or blood stagnates and resides for a prolonged time while blood is otherwise flowing through the system. Zones of fluid stagnation are especially found in the pressure measuring domes of the PRISMA™ system.

Extracorporeal blood treatment usually requires anticoagulation of blood. The reason for this is the activation of blood coagulation by shear and by contact of blood to the surface of the extracorporeal circuit. After activation of the clotting system, it takes several minutes until a clot forms. If a fluid path contains poorly perfused dead zones where blood stagnates for a longer period, then blood clots will form at these sites and the clots eventually will block the entire circuit. Other causes for the enhanced formation of blood clots are blood-air interfaces and obstructions in the fluid path, e.g., the commonly used "clot" filters in drip chambers.

Typically, systemic anticoagulation is used such that anticoagulants are not only in the blood in the extracorporeal circuit, but also in the blood in the patient's circulation. This use of anticoagulants increases the risk of bleeding by the patient during and after treatment. Local anticoagulation or anticoagulation free treatment has been reported, but is possible only with additional equipment and monitoring.

The common blood accesses for acute treatment with extracorporeal circuits are central venous catheters. The insertion and use of central venous catheters are related to several risks that may result in death or severe impairment. In particular, stenosis of the central vessels after use of catheters, which has been well documented, makes frequent insertion of central venous catheters impossible.

The use of peripheral vein access has not been reported with devices used for extracorporeal blood treatments, such as those described above. Peripheral veins tend to collapse during the withdrawal of blood by an extracorporeal blood circuit. The collapse of a vein would cause the blood circuit to issue frequent alarms that would require continuous observation by trained personnel. Also, extracorporeal systems for the use with adults are designed for blood flows not achievable with peripheral vein access.

SUMMARY OF THE INVENTION

An extracorporeal circuit has been designed having an optimized streamlined blood passage that is free of obstructions and dead zones where blood can stagnate. The circuit components, e.g., pressure sensors, in the blood are free of obstructions and do not cause blood to stagnate in the circuit or to undergo substantial flow speed changes. The circuit can be used to treat CHF by continuous filtration of blood using peripheral venous blood access, and with minimal or no anticoagulation.

The extracorporeal circuit may be characterized by the normalized residence volume method, derived from the residence time measurements. The normalized volume parameter is used to characterize the flow characteristics of an extracorporeal circuit independently of the total fluid volume capacity of that circuit. When using the 10% to 90% rise of the output function in the normalized volume diagram, the optimized extracorporeal circuit shows superior performance. The present extracorporeal circuit may be applied to remove excess fluid from a CHF patient allow treatment for up to eight hours using no or minimal anticoagulation.

A practical means to overcome the barriers for the effective treatment of CHF by mechanical fluid removal is described in U.S. application Ser. No. 09/618,759, filed Jul. 18, 2000, entitled "Method and Apparatus for Peripheral Vein Fluid Removal in Heart Failure", U.S. application Ser. No. 09/660,195 filed Sep. 12, 2000, entitled "Blood Pump Having Disposable Blood Passage Cartridge With Integrated Pressure Sensors," both of which patent applications are incorporated by reference.

SUMMARY OF THE DRAWINGS

A preferred embodiment of the invention, the setup for the characterization of hydraulic components by the normalized residence volume method as well as the results of such characterization for an extracorporeal system as described by the invention and for the extracorporeal circuit of the PRISMA device are illustrated in the attached drawings.

FIG. 8 shows the normalized residence volume calculation derived from a residence time measurement for the extracorporeal circuit of the PRISMA™ device.

DETAILED DESCRIPTION OF THE INVENTION

Figure 1A:
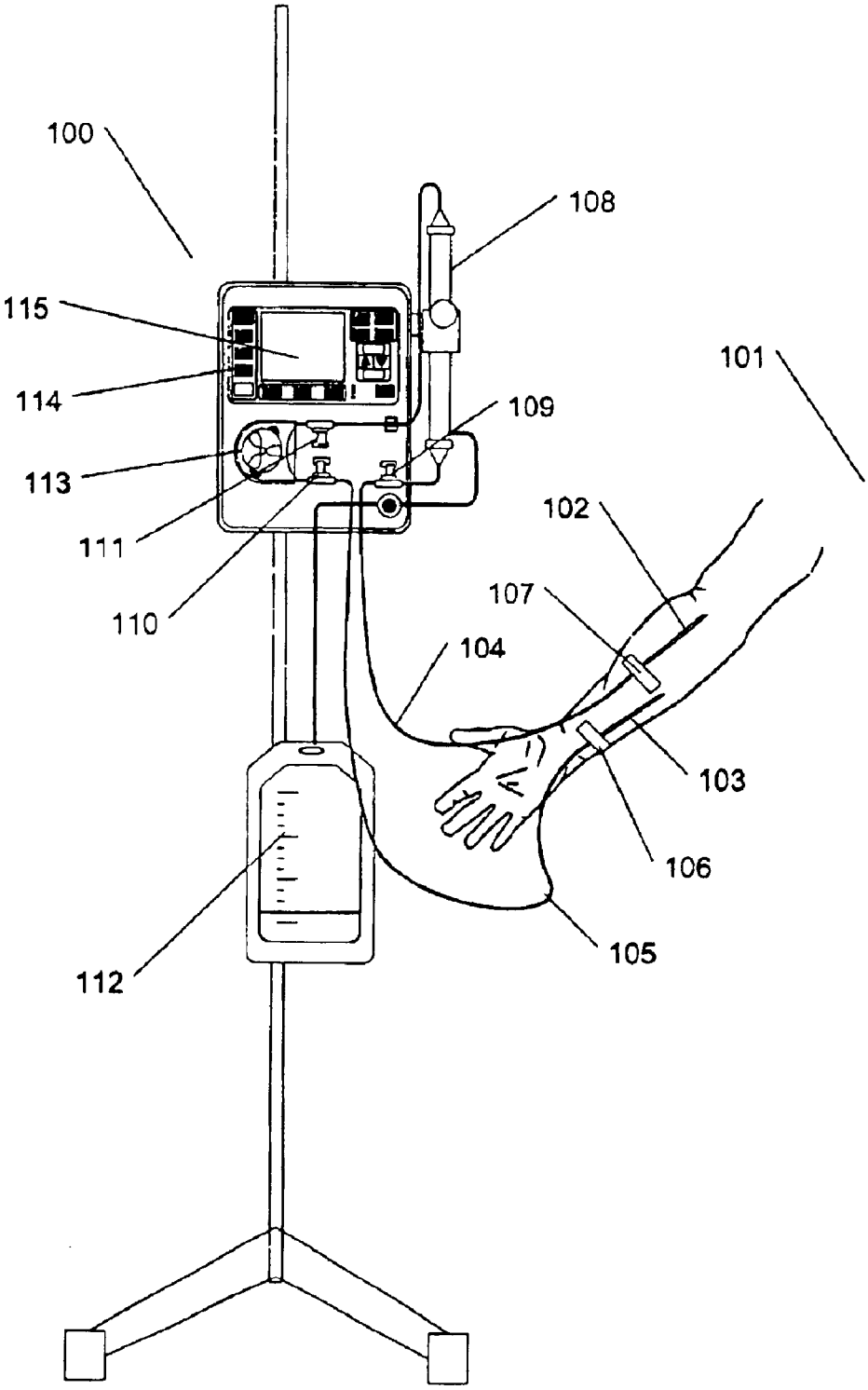
FIGS. 1A and 1B illustrate the extracorporeal circuit of an embodiment of the present invention.

FIG. 1A illustrates the treatment of a fluid overloaded patient with a blood treatment system 100. Patient 101 can undergo treatment while in bed or sitting in a chair. Patient can be conscious or asleep. To initiate treatment two relatively standard 18G needles 102 and 103 are introduced into suitable peripheral veins (on the same or different arms) for the withdrawal and return of the blood. This procedure is no different from blood draw or IV therapy. Needles and attached to tubing 104 and 105 and secured to skin with attachments 106 and 107. The blood circuit that consists of the blood filter 108, tubes, pressure sensors 109, 110 and 111 and the ultrafiltrate collection bag 112. The circuit is supplied in one sterile package and is never reused. It is easy to mount on the pump 113 and can be primed and prepared ready for operation within minutes by one person.

During operation, the present invention requires minimal intervention from user. User sets the maximum rate at which fluid is to be removed from the patient using the control panel 114. Ultrafiltrate is collected into a graduated one-liter collection bag 112. When the bag is full, ultrafiltration stops until the bag is emptied. Information to assist the user in priming, setup and operation is displayed on the LCD display 115.

Figure 1B:
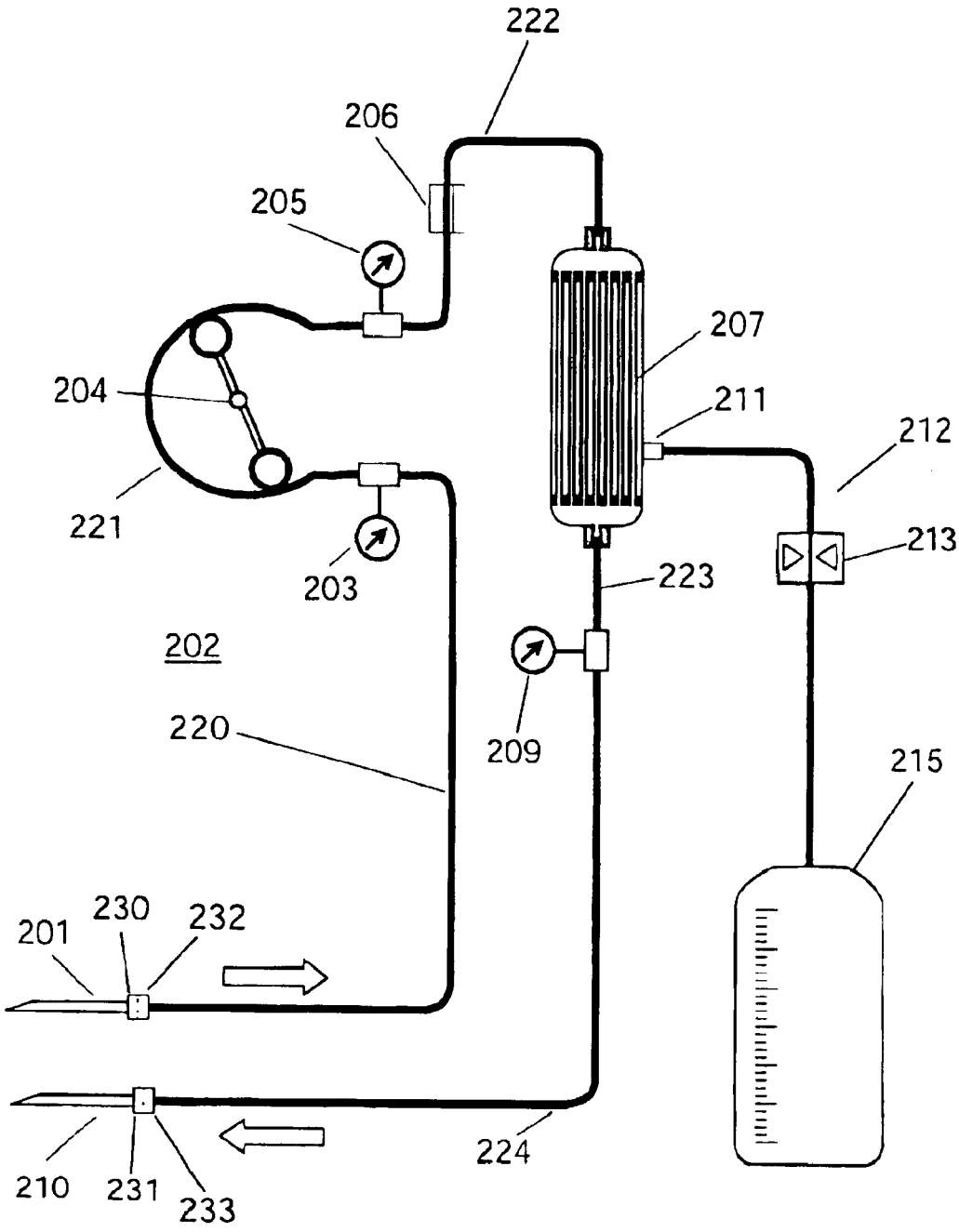

FIG. 1B illustrates the fluid path of an embodiment of the present invention. The embodiment consists of a disposable extracorporeal circuit for a treatment device comprising a peristaltic blood pump, protective systems a display and a microprocessor control unit.

Blood is withdrawn from the patient through the withdrawal needle assembly 201. Blood flow is controlled by a roller pump 204. The withdrawal needle assembly is connected to the blood tubing 220 by a pair of matching connectors 230, 232. Connector 230 is part of the withdrawal needle assembly and connector 232 is a part of the blood tubing 220. These connectors can either be an integral part of the connected blood tubing or separate parts glued, welded or mechanical fixated with the tubing.

Blood tubing 220 that is typically 2 m (meters) long is connected to a disposable pressure sensor 203. A suitable pressure sensor is disclosed in U.S. application Ser. No. 09/660,195 filed Sep. 12, 2000. The opposite end of the pressure sensor 203 is further connected to blood pump tubing 221 that is connected to the disposable pressure sensor 205. Pressure sensor 205 is connected to blood tubing 222 leading to and permanently connected to the inlet of the blood side of the hemofilter 207.

The outlet of the blood side of the hemofilter is connected to blood tubing 223 that is connected to one side of a disposable pressure sensor 209. The other side of the disposable pressure 209 is connected to the blood tubing 224 that ends with the connector 233. Connector 231 is part of the blood return needle assembly. A filtrate line 212 is connected to the filtrate outlet 211 of the hemofilter 207 on one side and to the filtrate collection bag 215 on the other side. An ultrasonic air detector 206 with sensors in contact with the outer surface of the blood tubing is included, but does not interrupt the smooth flow path in the circuit.

The blood passage in the extracorporeal circuit is an obstruction free smooth blood flow path throughout the circuit. There are no dead zones and no blood—air interfaces in the blood passage. The catheter needle assemblies 201, 210 are preferably designed such that the interface between the needle with a typical inner diameter of 1 mm is connected to the blood tubing with a typical inner diameter of 3 mm by a cone with a smooth blood passage having a cone angle of 100. Matching connectors 230, 232 and 231, 233 respectively are preferably designed such that the continuous blood flow path with a typical inner diameter of 3 mm is not interrupted. For convenience and for compatibility with existing systems, Luer-lock connectors could be used at this point although these connectors are not obstruction free.

Disposable pressure transducers are positioned in the flow path to be obstruction free and have essentially the same diameter as the blood tubing. To avoid kinking of the blood tubing leading from and to the patient, blood tubing 220 and 209 is preferably made from a harder tubing material than is the blood pump tubing 221. Blood tubing 222 and 223 can be made from either the harder or the softer variety of medical tubing material that is suitable for use in an extracorporeal blood circuit.

The filter 207 provides a smooth flow path for the blood through the filter passages. A membrane surface area of 0.1 $m^2$ may be used to provide sufficient fluid removal during operation of the extracorporeal circuit. A smooth flow path is achieved by making this filter long and thin, rather than short and thick as in the PRISMA design. The filter may have an effective length of 22.5 cm and a fiber bundle diameter of 1.2 cm.

A parameter for the characterization of the flow characteristic of an extracorporeal circuit or of its components is the residence time. This method of characterizing as extracorporeal has been described, e.g., by Cooney D O, Infantolino W, Kane R. in "Comparative Studies of Hemoperfusion Devices". For a passive extracorporeal device, the total residence time of the blood in the device should be minimized to reduce the potential for clotting.

Pressure drop and flow uniformity tests may also be used to characterize the blood flow through an extracorporeal circuit, especially those that filter fluids and/or solutes from blood. See Biomater Med Devices Artif Organs 1979;7:443–54. In this method the device to be investigated is sequentially perfused with two fluids with different properties. A step function is produced at the input when the fluids are switched and the resulting function at the output is recorded as a function of time. For an ideal flow, the output function would be a step function as well. In an ideal filter, all portions of the filter membrane are being perfused uniformly. In an ideal filter, the blood is thickened (due to fluid being removed by the filter) uniformly as it passes through the capillaries of the filter. In a non-ideal filter, the slope of the step-function deviates from the ideal slope because blood moves faster in some capillaries than in others, and/or the blood is thickened less in some capillaries than others. The blood becomes more concentrated and has a higher viscosity in those filter capillaries with slow perfusion, than in other capillaries that have at least an average flow rate of blood. These non-uniformities in the blood flowing through a filter can be indicated by the slope of the step-function curve. Deviation from the ideal slope indicates non-uniform thickening of the blood and non-uniform blood viscosity. The deviation of the output function from a step function can be used as a measure for the quality of the flow design.

Figure 2:
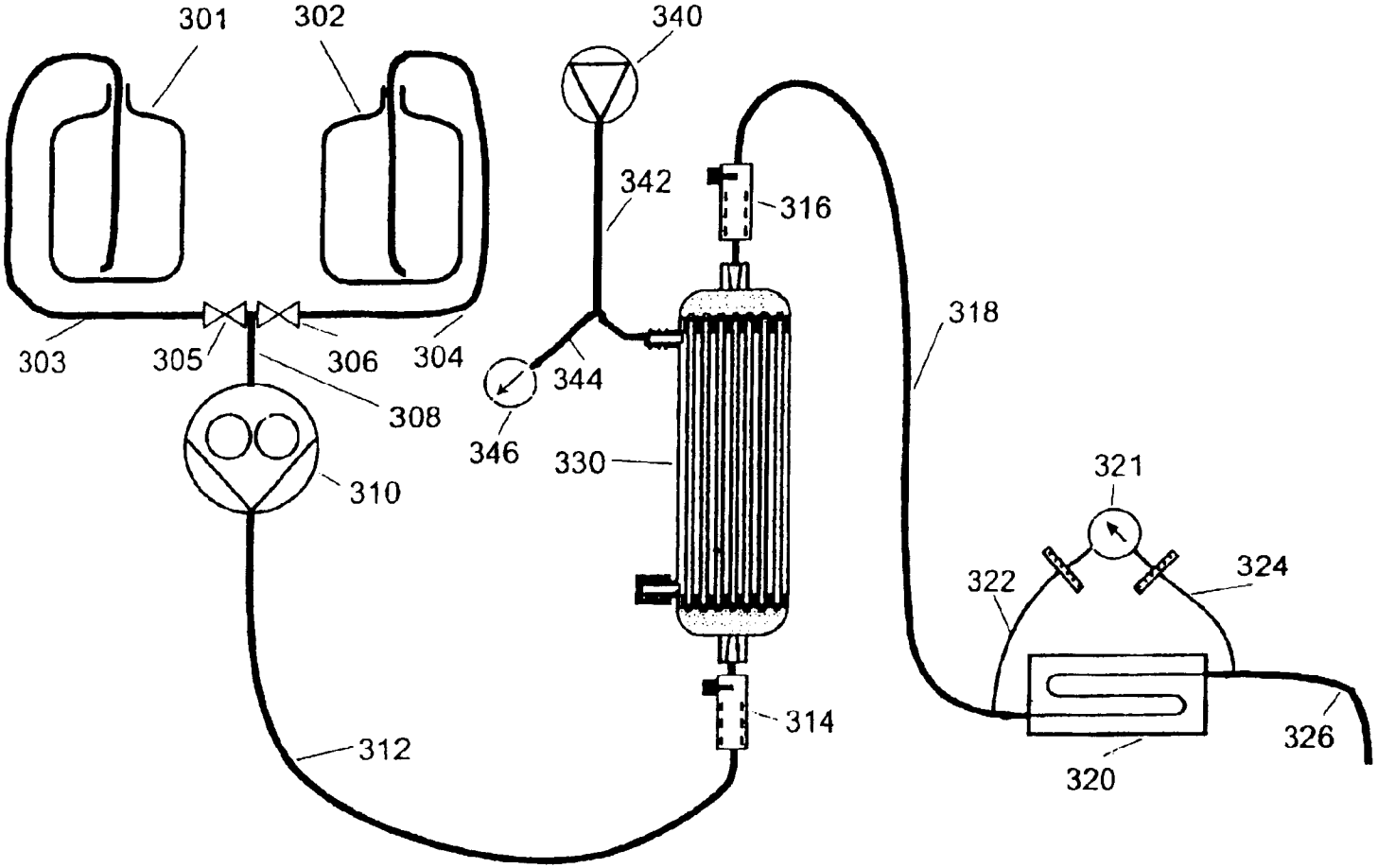
FIG. 2 illustrates the flow diagram employed for the measurement of the residence time function.

FIG. 2 shows a flow diagram of a test setup that can be employed to determine the characterization of extracorporeal circuits or its elements. Bag 301 is a carboy containing demineralized water with a conductivity of typically 5 $\mu$S/cm (microSiemens per cm). Container 302 contains a salt solution (sodium chloride solution) with a typical conductivity of 30 mS/cm. The container 301 is connected through a conduit 303 with the valve 305. The container 302 is connected to the valve 306 through conduit 304. Valves 305 and 306 are connected with a T to conduit 308 leading to a gear pump 310.

A gear pump 310 is connected to a first temperature compensated conductivity sensor 314 by conduit 312. A test object 330, e.g., a filter or blood path in an extracorporeal circuit, is connected to the first conductivity sensor 314 on one side and the second temperature compensated conductivity sensor 316 on the other side. The outlet of the second conductivity sensor 316 is connected to a mass flow meter 320 through conduit 318, and from the mass flow meter 320 a conduit 326 leads to drain. The pressure drop of the mass flow meter 320 is measured by pressure sensor 321 connected to inlet and outlet of the mass flow meter 320 by lines 322 and 324 respectively. If the test object is a filter or if a filter is part of the test object as shown in FIG. 2, the filtrate side is connected to an air pump 340 through a conduit 342, from conduit 324 a pressure measuring line 344 leads to a pressure sensor 346.

An air pump 340 allows removal of fluid from the filtrate side of the filter 330. Fluid in the blood passage side of the filter is pushed through the membrane if the air pressure is higher than the maximum fluid pressure on the fluid (blood) side of the membrane. Because the membrane is hydrophilic, air cannot pass the membrane as gas. Fluid, however, remains in the pores of the membrane. The purpose of this fluid removal from the filtrate side is to avoid any influence from the filtrate space. During the measurement, sodium and chloride ions can diffuse freely through the membrane. With a fluid filled filtrate space the measurement would include the filtrate side that would lead to wrong conclusions about the fluid distribution on the "blood" side.

Conductivity sensors 314, 316 and optionally pressure sensors 321 and 346 are connected to a computer for continuous recording of the signals as function of time. To record the residence time, the function valve 305 is opened and pump 310 operated at a prescribed speed, e.g., 100 mL/min. A baseline value of ~5 $\mu$S/cm is established, based on readings from conductivity sensors 314 and 316. Next, a continuous recording of the signals from conductivity sensors 314 and 316 is started. Also, valve 305 is closed and valve 306 is opened. Fluid with a conductivity of ~30 mS/cm flows through the pump 310 to the conductivity sensor 314 causing an increase of the signal as shown by signal tracing 404 in the graph 401 of FIG. 3. The conductivity sensor 316 at the outlet records a similar but less steep signal after some delay in time depending on the filling volume of the test object 330 and the flow speed of the pump 310. The signal tracing of the conductivity sensor 316 is shown as 406 in FIG. 3. In case the test object contains a filter air pump 340 is employed to pressurize the filtrate side with air at a pressure exceeding the maximum fluid pressure on the blood side of the filter prior to the start of the measurement. This forces all fluid from the filtrate side to the blood side limiting the fluid volume to the fluid volume of the blood path and the fluid volume trapped in the membrane pores.

Figure 3:
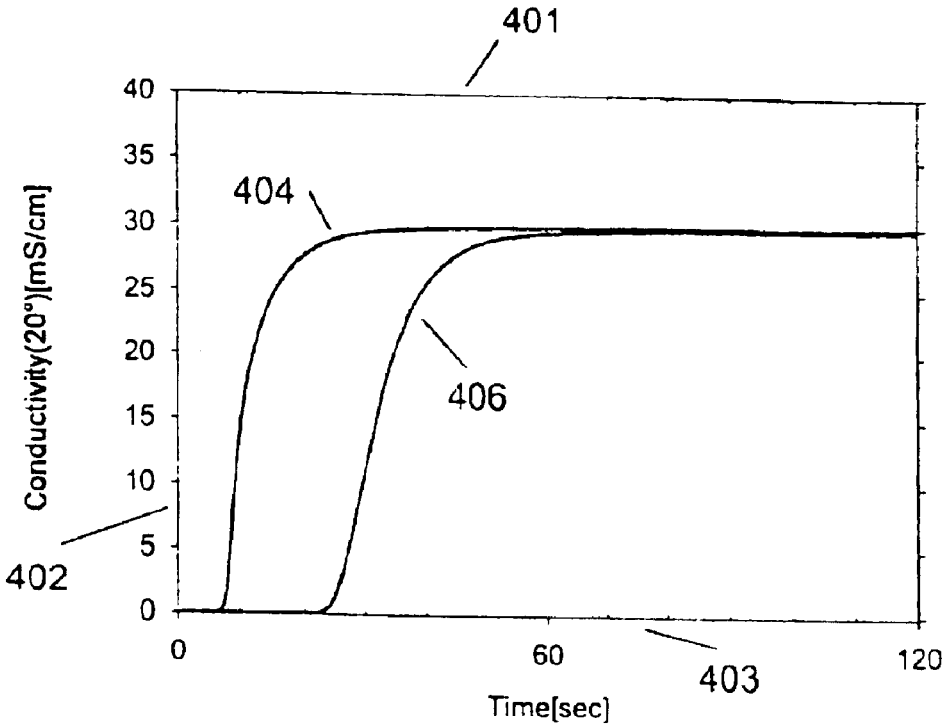
FIG. 3 is a graph showing the result of a residence time measurement with conductivity sensors.
Figure 4:
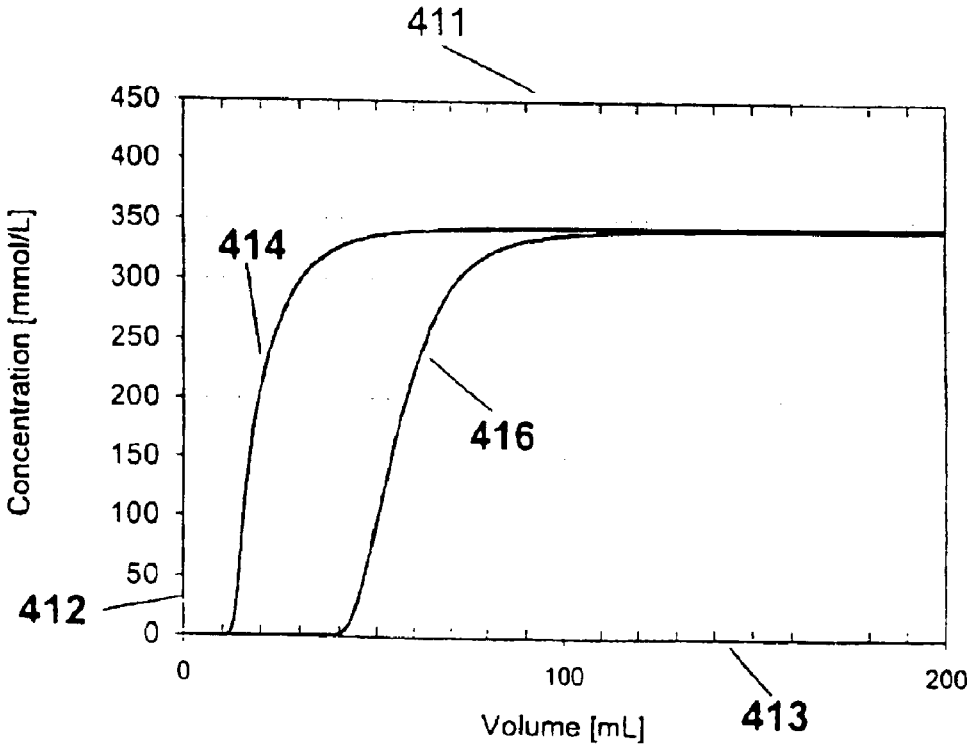
FIG. 4 is a graph showing the conversion of the graph 3 data from the conductivity versus time domain into the concentration versus volume domain.

FIG. 3 includes a diagram 401 that is mathematically converted into the diagram 411 shown by FIG. 4 by the following steps: Conductivity 402 is converted into concentration 412 by employing a five order power function derived from tables published in the CRC handbook of chemistry and physics $65^{th}$ edition for sodium chloride. The time axis 403 is converted into a volume axis 413 by multiplying the time increments between the discrete points of measurement with the corresponding flow values and summation. The results are the input sensor function 414 and the output sensor function 416 in the concentration versus volume domain.

Figure 5:
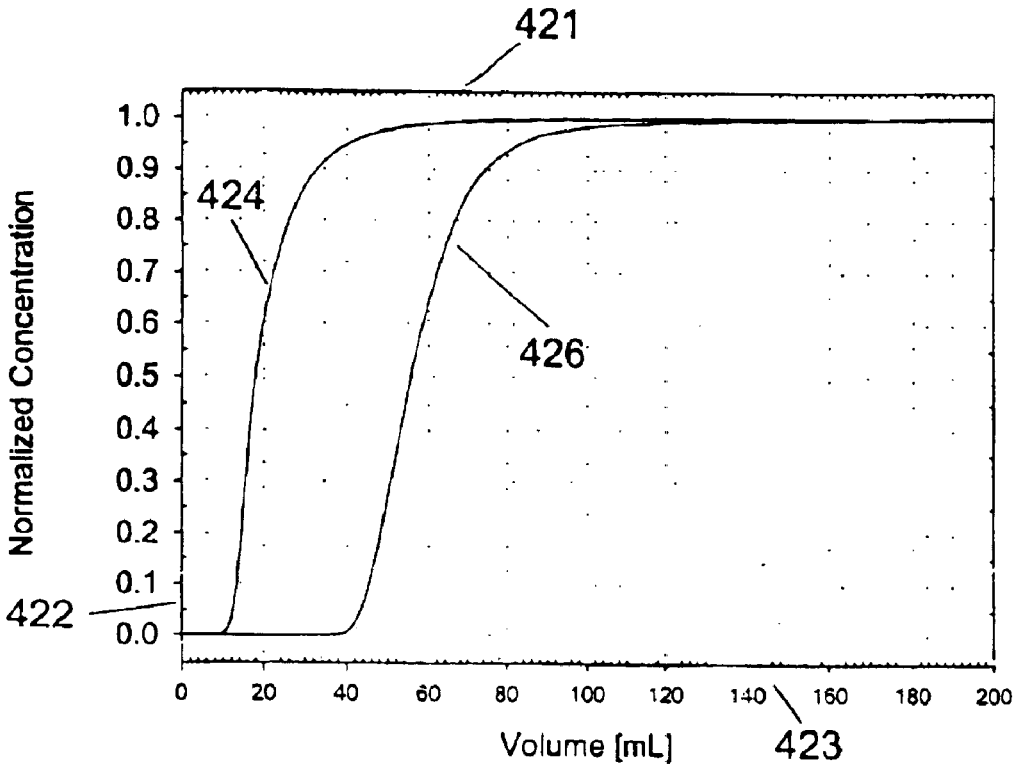
FIG. 5 is a graph derived from the graph of FIG. 4 by the normalization of the concentration axis with the maximum concentration measured that is the concentration in carboy 302.

FIG. 5 shows a diagram 421 mathematically derived from the graph 411 of FIG. 4 by normalizing the concentration axis 412 with the maximum concentration measured. This concentration is equal to the concentration in carboy 302 within the errors of measurement. The result is a graph in the normalized concentration 422 versus volume 423 domain with 424 being the input function and 426 being the output function.

Figure 6:
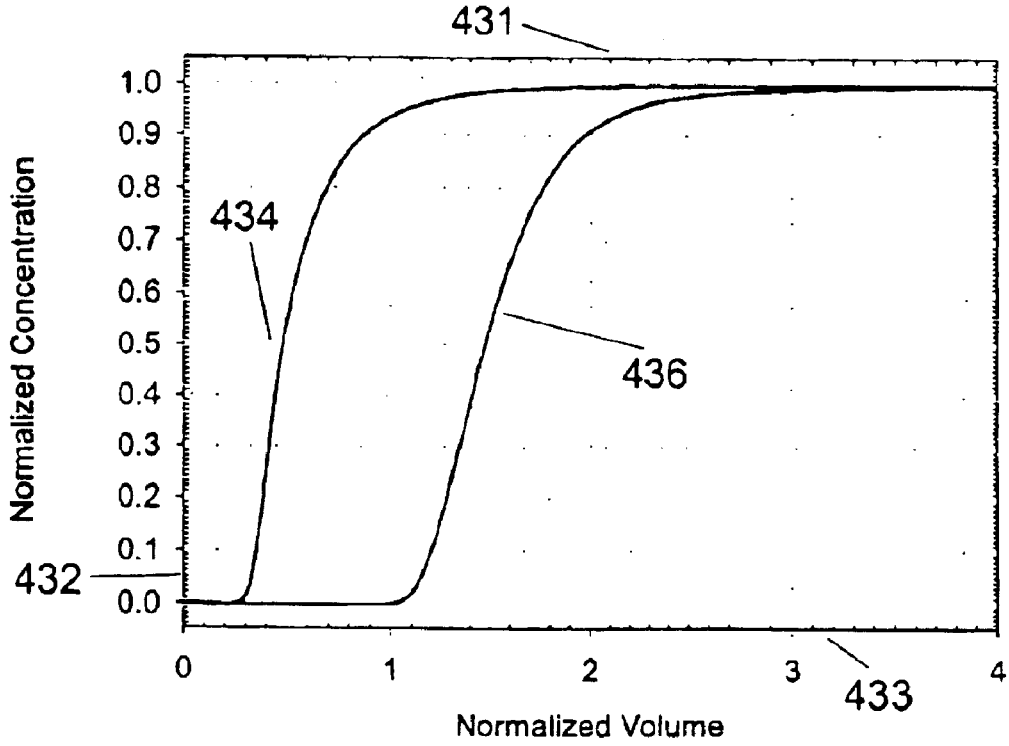
FIG. 6 is a graph derived from the graph of FIG. 5 by the normalization of the volume axis with the volume of the test object calculated from the graph of FIG. 5.

FIG. 6 shows a diagram mathematically derived from the graph 421 of FIG. 5 by normalizing the volume scale 423 with the calculated volume of the test object. The volume of the test object is calculated from the graph 421 of FIG. 5 by subtracting the integral under tracing 424 from the integral under tracing 426 over the volume interval shown in the graph of FIG. 5. The result is the graph 431 in the normalized concentration 432 versus normalized volume 433 domain with 434 being the input function and 436 being the output function.

Figure 7:
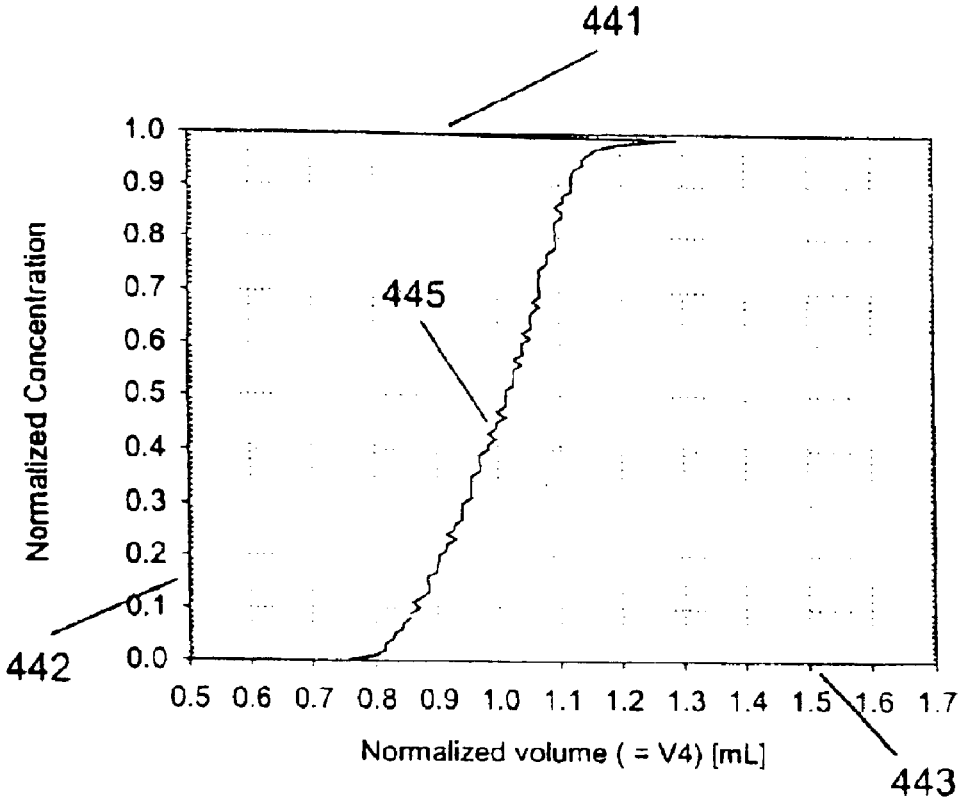
FIG. 7 is a graph derived from the graph of FIG. 6 by eliminating the effect of the time course of the input conductivity/concentration function. The input fraction is a step function at zero normalized volume. The test object characterized by this figure is the extracorporeal circuit described by this invention.

FIG. 7 shows the result of the final step of the derivation in graph 440. The delay time and non-ideal step function of the input signal 434 is removed by subtracting the normalized volume between start and tracing 434 for discrete values of the normalized concentration from the corresponding normalized volume of the tracing 436 by employing a lookup table. The lookup table is constructed in 1% intervals of the normalized concentration. This procedure results in the tracing 445 of graph 441 showing the output function for an extracorporeal circuit as described by the invention for an ideal step function at normalized volume 0 at the input.

Figure 8:
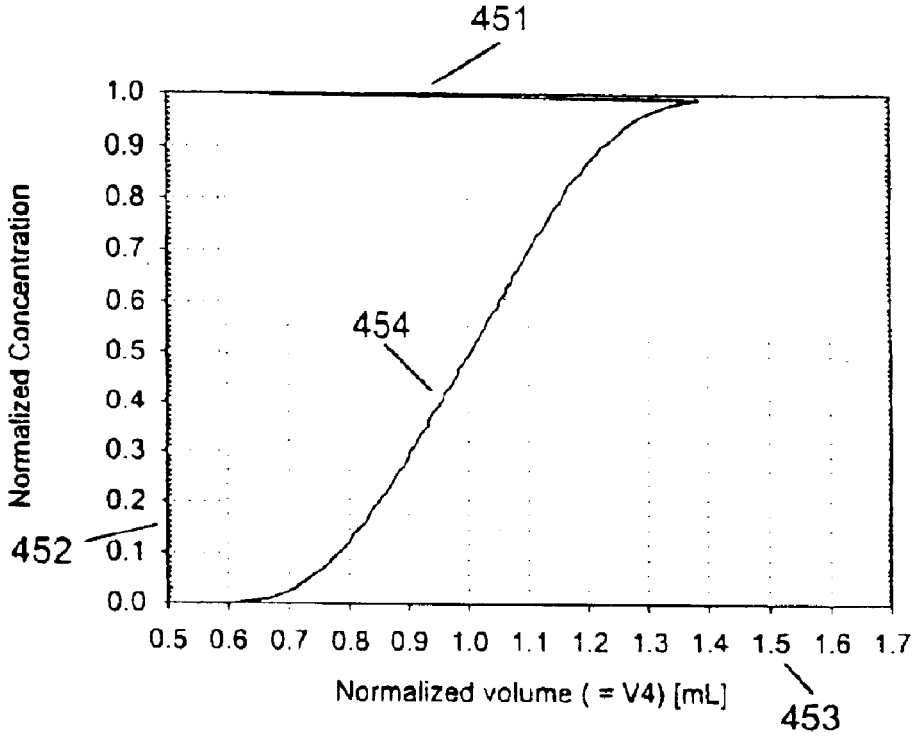
FIG. 8 is a graph similar to the graph in FIG. 7. The test object characterized by this graph is the extracorporeal circuit of the PRISMA™.

FIG. 8 shows the result of the measurement and derivation equivalent to the steps described for FIGS. 3 to 7 but for the extracorporeal circuit of the PRISMA. The graph 451 (where the normalized concentration 452 is the vertical axis and the normalized volume 453 is the horizontal axis) shows the tracing 454 in the normalized volume 453 versus normalized concentration 452 domain. The described data has been recorded employing the program LabView (National Instruments). The recorded data has been imported into SigmaPlot 5.0 (SPSS, Inc.) and the mathematical conversions described above were done with the transform program written for SigmaPlot shown in the appendix.

Comparing graphs 441 and 451 allow for a comparison of extracorporeal circuits independent of the absolute volume and the blood flow. For the quantitation of the 10% to 90% interval is used as shown in the following table:

| Relative volume | Data from FIG. 7 (Invention) | Data from FIG. 8 (PRISMA) |
|---|---|---|
| 10% | 0.87 | 0.78 |
| 50% | 1.01 | 1.00 |
| 90% | 1.02 | 1.22 |
| 90%–10% | 0.15 | 0.44 |

The 10% to 90% rise time is more than twice as large for the PRISMA compared to the optimized extracorporeal circuit according to the invention. The volume calculated for the two systems was 37.09 mL for the system according to the invention and 105.38 for the PRISMA. As mentioned above, this volume includes the fluid trapped in the porous structure of the microporous fibers of the filters. This volume is larger than the volume measured by blowing out fluid with air. Normalization of the data as described above nevertheless allows the direct comparison of the flow properties independent of the absolute size and volume of the system.

From graphs 441 (FIG. 7) or 451 (FIG. 8) and the volumes the residence time can easily be calculated. For the extracorporeal circuit according to the disclosed embodiment of the invention the volume is ~37 mL. r 128 sec a factor of 3.5 large. For a flow of 60 mL/min typical for peripheral flow, the resulting residence time for the 90% concentration point (1.12) is 1.12*37/60=0.69 min or ~41 sec. For the same flow the 90% residence time for the PRISMA is 1.22*105/60= 2.13 min or 128 sec a factor of 3.5 larger.

In an exemplary embodiment, FIGS. 1A and 1B illustrate the operation and fluid path of the blood treatment system 100 of a microprocessor controlled console and a disposable kit. Disposable kit is bonded (with the exception of needles) and is supplied sterile.

Blood is withdrawn from the patient through the 18 Gage or similar withdrawal needle 102. The needle 102 is inserted into a suitable peripheral vein in the patient's arm. Blood flow is controlled by the roller pump 113. Before entering the pump blood passes through approximately two meters of plastic tubing 104. Tubing is made out of medical PVC of the kind used for IV lines and has internal diameter (ID) of 3 mm. Pump 113 is rotated by a DC motor under microprocessor control. The pump segment (compressed by the rollers) of the tubing has the same ID as the rest of the blood circuit. The system is designed so that approximately 1 mL of blood is pumped per each full rotation of the pump, e.g. pump speed of 60 RPM corresponds to 60 mL/min.

The disposable withdrawal pressure sensor 109 is a part of the blood circuit. Pressure sensor 109 is a flow-through type commonly used for blood pressure measurement. There are no bubble trap or separation diaphragms in the sensor design, which reduce the accuracy. Pressure sensor is designed to measure negative (suction) pressure down to −400 mmHg. All pressure measurements in the fluid extraction system are referenced to atmospheric. The withdrawal pressure signal is used by the microprocessor control system to maintain the blood flow from the vein. Typically, a peripheral vein can continuously supply 60–100 mL/min of blood. This assumption is supported by the clinical experience with plasma apheresis machines.

In some cases, blood flow can be temporarily impeded by the collapse of the vein caused by the patient motion. In other cases the vein of the patient may not be sufficient to supply the maximum desired flow of 60 mL/min. The software in the present invention microprocessor is designed to control the withdrawal of blood to prevent or recover from the collapse of the vein and reestablish the blood flow based on the signal from the withdrawal pressure sensor.

The same pressure signal from the sensor 109 is used to detect the disconnect of the withdrawal bloodline 104 from the needle 102. This condition is detected by the abrupt decrease of the withdrawal pressure generated by the pump. The resistance of the 18 Gage needle, which is 4 cm long with an approximately 0.8 mm ID at a flow rate corresponding to a 60 mmHg, pressure drop is on the order of the 100 mmHg. The resistance of 2 meters of blood tubing with a 3.5 mm ID at the same flow rate is on the order of 20 mmHg. This enables automatic reliable detection of the line disconnection. The occlusion of the withdrawal bloodline is detected in the similar fashion. The occlusion can be caused by the collapse of the vein or by the kinked blood tube. Occlusion results in a rapid decrease (more negative) of the pump suction pressure that is detected by the microprocessor. In response to this condition, the microprocessor stops the pump and alarms the user.

A double roller pump 113 may be used to pump blood. As the pump 113 rotates, rollers compress the segment of PVC tubing and generate flow. Pump is adjusted to be fully occlusive until the pressure limit is reached. The rollers are spring loaded to limit the maximum positive and negative pressure generated by pump head. This feature is not normally used to limit pressure in the circuit and is only included as a secondary safety precaution.

A direct drive stepper motor rotates the rollers, and the speed of the motor is determined by the controller microprocessor. The RPM of the pump 113 is used as a feedback signal by the controller to determine the blood flow. Normal operational blood flow in the present invention is between 40 and 60 mL/min. This minimum rate of blood flow is needed to generate Trans Membrane Pressure (TMP) needed for ultrafiltration and to prevent stagnation and clotting of blood in filter 207.

Pump pressure sensor 205 is incorporated into the post-pump segment of the blood tubing connecting pump 204 to the blood inlet line 104 coupled to the filter 207. Like other pressure sensors in the present invention, it is a flow through device that does not create a blood-air interface and does not disturb the blood flow. The pump pressure signal is used by the microprocessor to determine TMP used to calculate the ultrafiltration rate. It is also used to detect abnormal conditions in the circuit such as occlusion or unacceptable clotting of the filter and disconnection of the blood line between the pump 204 and the filter 207.

On its way from the pump 204 to the filter 207, blood passes through the air detector 206. The air detector 206 is of ultrasonic type and can detect air in amounts exceeding approximately 50 microliters. The detector 206 uses technology based on the difference of the speed of sound in liquid and in gaseous media. If an air bubble is detected, the pump 204 is stopped almost instantaneously (within few milliseconds). The bubble detector output signal is hard wired into the motor control logic and the pump 204 is stopped independently of the microprocessor control if a bubble is detected.

Air can only enter the present invention circuit from the pre-pump (negative pressure) segment of the blood circuit 202. All the rest of the circuit downstream of the pump 204 is always pressurized. For this reason, the bubble detector is placed before the filter.

Blood pressure in the post pump, pre-filter segment of the circuit is determined by the patient's venous pressure, the resistance to flow generated by the return needle 210, resistance of hollow fibers in the filter assembly 207 and the resistance of interconnecting tubing 224. At blood flows of 40 to 60 mL/min the pump pressure is in the 300 to 500 mmHg range depending on the blood flow, condition of the filter, blood viscosity and the condition in the patient's vein.

The filter 207 is a main component of the present invention. Inside the filter 207 the ultrafiltration occurs. Whole blood enters the bundle of hollow fibers from the connector on the top of the cap of the filter canister. There are approximately 700 hollow fibers in the bundle, and each fiber is a filter. Blood flows through a channel approximately 0.2 mm in diameter in each fiber. The walls of the channel are made of a porous material. The pores are permeable to water and small solutes but impermeable to red blood cells, proteins and other blood components that are larger than 50,000–60,000 Daltons. Blood flow in fibers is tangential to the surface of the filter membrane. The shear rate resulting from the blood velocity is high enough such that the pores in the membrane are protected from fouling by particles, allowing the filtrate to permeate the fiber wall. Filtrate (ultrafiltrate) leaves the fiber bundle and is collected in space between the inner wall of the canister and outer walls of the fibers.

The geometry of the filter is optimized to prevent clotting and fouling of the membrane. The active area of the filter membrane is approximately 0.1 $m^2$. The permeability KUF of the membrane is 30 to 33 mL/hour/$m^2$/mmHg. These parameters allow the desired ultrafiltration rate of approximately 500 mL/min at the TMP of 150 to 250 mmHg that is generated by the resistance to flow. The effective filter length is 22.5 cm and the diameter of the filter fiber bundle is 1.2 cm. This results in the shear rate of 1,200 to 1,800 $sec^{-1}$ at the blood flow rate of 40 to 60 mL/min.

The TMP is the present invention is defined predominantly by the resistance of the return needle 210 and the resistance of the filter bundle inside the filter 207. The properties of the filter 207 and the needle 210 are selected to assure the desired TMP of 150 to 250 mmHg at blood flow of 40–60 mL/min where blood has hematocrit of 35 to 50% at 37° C.

The quantitative clinical goal was formulated for the apparatus being developed in terms of fluid removal. Applicants' research established that for the fluid removal device to be clinically useful it should remove water at the rate of 100 to 500 mL/hour. Lower rates of fluid removal are only required in hemodynamically unstable patients that are treated in the ICU and are not the targeted patient population. Fluid removal rates higher than 500 mL/hour (theoretically as high as 1,000 mL/hour) may be practical in some patients but are expected to be too high risk in the majority. It is only advisable to remove water from blood at the rate at which fluid can be recruited from tissue. Higher rates may lead to hypotension.

Blood hematocrit (volume fraction of red blood cells) in CHF patients is expected to be in the range of 30 to 40% of the total blood volume. It is possible to condense the filtered blood to the hematocrit range of 50% to 60% and still be able to return blood through a standard needle. Therefore, extraction of approximately 20% to 30% of volume from blood as water is possible. Assuming this extraction rate, the amount of blood removed from a peripheral vein is less than 2% of the total cardiac output. In addition, at this extraction rate, the potential ultrafiltrate flow may be as much as 1 L/hour. Alternatively, a lower extraction rate, e.g., 0.1 liter/hour, may be selected. At the blood flow rate of 60 mL/min applicants successfully extracted up to 12 mL/min (or 720 mL/hour) of ultrafiltrate in the laboratory using the filter described in this invention. Therefore, it is possible to consistently extract the required 500 mL/hour of water from the blood flow withdrawn and returned into a peripheral vein.

Applicants established that the much higher blood flows that are used in adults by all existing renal replacement therapy machines and particularly by machines for acute CVVH treatment of CHF patients are necessitated by the filter designed to remove solute and more specifically by the relatively high surface area of the filter. This large surface area is needed for solute removal. If the goal of treatment was to remove water only, high blood flow will still be needed to reduce the time of exposure of blood to the synthetic membrane and to prevent clotting.

Another important consideration that forces the designers of CVVH machines to use high blood flow and consequentially the central venous access is the need to maintain substantially high wall shear rate of blood flowing inside the filter capillaries (hollow fibers). Flow of blood inside a fiber is laminar. Shear rate at the wall can be calculated using the simple Equation 1:

$$y=32\times Q/(d^3\times pi) \qquad \text{(Equation 1)}$$

Q is blood volumetric mass flow rate and "d" is the internal diameter of the capillary.

The ultrafiltration rate is influenced by membrane fouling which is an equilibrium of wall shear rate and ultrafiltration rate per unit surface area. With the increasing surface area the wall shear rate will decrease unless the blood flow is increased to compensate. It becomes apparent from literature that the wall shear rate should be 1,000 $sec^{-1}$ or higher to achieve sufficient filtrate flux at high hematocrit. It is also known from literature that the high shear rate in excess of 2,500 $sec^{-1}$ is undesirable since it can cause hemolysis and damage to red blood cells. At the same time, it is apparent that the surface area and size of the filter should be minimized. Biocompatibility is inversely proportional to the surface area exposed to blood. The likelihood of clotting increases with residence time proportional to the filling volume. Also, cost of a smaller filter is lower.

To minimize the cost of the filter, the use of commercially-available fibers with optimized biocompatibility and consistent filtration properties is desired. Suitable filter fiber is available, for example, from Minntech Inc. in Minnesota. Each fiber has internal diameter of 0.2 mm. Pores in the fiber walls are optimized to retain solutes of greater than 50,000 Daltons. The permeability of this fiber is 33 mL/hour/$m^2$/mmHg. If a membrane with total surface area of only 0.1 $m^2$ is constructed from this fiber, the resulting theoretical ultrafiltration rate will be 330 mL/hour at TMP of 100 mmHg and 660 mL/hour at TMP of 200 mmHg. These numbers are consistent with the objective of the design.

To calculate the KUF of the filter, the permeability of fiber is multiplied by the surface area of the membrane. Therefore KUF filter=33×0.1=3.3 mL/hour/mmHg.

It is known from literature that the blood flow is not equal between the fibers in the filter bundle. Blood flow and consequentially the wall shear rate tends to be lower in the fibers closer to the periphery and higher in the central ones. Accordingly, blood residence time is longer in peripheral fibers. It is known from the practice of dialysis that the peripheral fibers tend to clot first.

To reduce the extracorporeal blood volume and the time that blood resides outside of the body it is desired to use blood lines that have internal diameter as small as practical without creating excessive resistance to flow. For our application, an internal diameter of around 3.0 mm is well suited. When blood exits the tubing and flows into the fiber bundle the diameter of the channel through which blood flows increases substantially. This creates turbulence and stagnant zones at the entrance into the bundle. These factors increase the probability of lotting.

It is therefore beneficial to design a filter that has a minimal but still practical diameter of the fiber bundle. This is achieved by reducing the number of fibers and increasing the length of the bundle. This approach is limited by two constraints. Resistance of the bundle to flow increases in proportion to the bundle length. Also, long filters substantially in access of 20–25 cm are difficult to manufacture and cumbersome to use.

Applicants chose to use a maximum length of the filter that is practical from the manufacturing standpoint. The resulting working length of the bundle is 22 cm (centimeters). To ensure the required surface area of the membrane, approximately 620 to 720 fibers of this length are need to be bundled in parallel. Assuming the fiber density of approximately 630 capillaries per $cm^2$ the diameter of the bundle is 1.2 cm. Such filter can be easily manufactured using existing methods and equipment. At the blood flow of 40 to 60 mL/min and blood hematocrit of approximately 40%, the resistance of this filter to blood flow is on the order of 100 to 200 mmHg. This pressure level is acceptable for the design of a circuit with a standard peristaltic pump and an 18 to 20 Gage (internal diameter of 0.8–1.0 mm) return needle.

Applicants overcame the perceived impossibility of clinical peripheral vein ultrafiltration that limited the use of mechanical fluid removal in CHF patients outside of the ICU environment. Applicants did this by drastically reducing the filter membrane surface area compared to common dialysis or CVVH filters to maintain high shear rate and low blood residence time. Specifically, a filter with the membrane surface of less than 0.2 $m^2$ and preferably 0.05 to 0.15 $m^2$ can remove the desired 100 to 700 mL/hour of water from the extracorporeal blood flow of less than 100 mL/min or more specifically of 40 to 60 mL/min with an average blood cell residence time outside the body of less than 2 minutes, and may be less than 1 minute. Although the filter is made of high permeability fiber due to the small surface area the KUF of the filter is less than 5 mL/hour/mmHg or preferably 2 to 4 mL/hour/mmHg. Typical filters used in adult patients have KUF of 30 to 50 mL/hour/mmHg. The much lower KUF gives the present invention device design an advantage of inherently safer operation. Food and Drug Administration (FDA) classifies all filters with KUF greater than 8 mL/hour/mmHg as "high permeability dialyzers". According to current FDA safety standards these devices have to be labeled for use only with ultrafiltration controllers that are independent of TMP based ultrafiltrate rate calculation. A small error of TMP measurement or a deviation of membrane permeability from the specification can result in substantial over or under filtration. The use of a low KUF filter enables, if desired, the present invention to avoid using a cumbersome and expensive ultrafiltration controller that typically involves a scale balance and an ultrafiltration pump.

A filter that is relatively long and narrow may optimize the blood flow inside the filter, maintain the desired wall shear rate and minimize membrane fouling and filter clotting. A filter with a fiber bundle that is approximately 20 cm long and 1.5 cm in diameter is particularly well suited for the application and is practical for manufacturing.

Filters for ultrafiltration of blood with small surface area of less than 0.2 $m^2$ are known. Example of such filter is Miniflow™ 10 from Hospal. Miniflow has surface area of 0.042 $m^2$ and KUF of 0.87 mL/hour/mmHg. All such filters without exception are used for hemofiltration therapy in neonatal patients and infants. The clinically used amount of blood flow through these filters is within the range that we targeted or 10 to 60 mL/min. Nevertheless, this amount of flow—if expressed as a fraction of the cardiac output for infants—is the same as the blood flow used in adult hemofiltration. Consequently, these infant filters are used with the central and not peripheral venous access.

To minimize clotting and fouling of the membrane it is desired to maintain substantially high blood flow through the filter even if the desired ultrafiltration rate is low. In traditional machines for renal replacement therapy it is typically achieved by reducing the TMP. Flow of ultrafiltrate is actively controlled by the roller pump in the ultrafiltrate removal line between the filter and the ultrafiltrate collection bag. When the pump is slowed down ultrafiltrate flow is retarded, pressure gradient across the membrane is reduced and ultrafiltration is slowed to the desired level. Alternatively, if the pump RPM is increased, the flow of ultrafiltrate is accelerated. Negative pressure can be developed by the pump to actively suck the ultrafiltrate across the membrane. For reasons of safety and simplicity, it was desired to have a machine that can reduce the ultrafiltration rate at the user command without an ultrafiltrate pump. For our preferred embodiment we used the duty cycle controlled ultrafiltration. A simple pinch valve is placed in the ultrafiltrate line. When the valve is closed, pressure across the membrane quickly equilibrates, and no ultrafiltration occurs. When the valve is opened, ultrafiltration occurs at the rate determined by the TMP and the KUF of the membrane. This rate can be calculated by the controller. Valve is cycled approximately every minute. The fraction of the cycle during which the valve remains opened determines the average rate at which fluid is removed.

Since the system embodying the present invention does not employ an ultrafiltrate pump that can create subatmospheric pressure on the ultrafiltrate side of the membrane, a simple and reliable method of controlling the total amount of fluid removed in one treatment iteration is possible. The ultrafiltrate is collected into a sealed bag that is connected by a tube to the ultrafiltrate collection chamber of the filter casing. During the treatment the bag is gradually filled up with fluid. It is desired to have a bag that has a relatively small volume and specifically volume of 0.5 to 1.5 liters. When the bag is full and its walls are fully distended, the pressure in the bag will start to rise until it is equal to the average pressure of blood inside the filter capillaries. Although some circulation of fluid is still possible in and out of fibers the net loss of fluid is zero. Until a nurse empties the bag, no removal of fluid is possible.

Pressure sensors are used in the blood circuit to alarm the disconnection and occlusion of blood lines. The pre- and post-filter pressure signals are also used to calculate TMP and ultrafiltration rate. Two types of pressure measurement devices are typically used in machines for renal replacement therapy.

Machines such as BP11 from Baxter use disposable air filled separation or drip chambers that are connected to permanently installed pressure sensors that are the part of the machine. This design introduces potentially hazardous air into the circuit. Air can cause embolism and accelerated clotting. Also, this type of measurement is affected by gravity.

Machines such as Prisma from Gambro use flexible silicone diaphragms to transmit blood pressure to sensors once again mounted on the apparatus itself. This method overcomes the deficiencies of drip chambers. Separation diaphragms are subject to error when the travel of a diaphragm is restricted. This necessitated a complicated diaphragm positioning system if the system is used for a substantial duration of time. Also, a substantial area of a diaphragm (typically 2–3 cm in diameter) is required to ensure reliable transmission of pressure. At a low blood flow it is likely that a stagnant zone will form inside the diaphragm chamber that will eventually lead to clotting.

The present invention utilizes flow through disposable pressure sensors. This sensors are a part of the disposable blood circuit. They do not disturb the laminar blood flow inside the blood line since the internal diameter of the sensor element is the same as of the blood tubing (3 mm). The sensing element is less than 2 mm in diameter and is embedded flush in the wall of the sensor housing. The housing is bonded flush with the internal wall of the blood line tube to form a continuous channel. Although similar disposable blood pressure sensors (such as ones made by Merit Medical of Utah) are used widely for invasive blood pressure measurement this design has never been previously used in an apparatus for fluid removal.

The present invention is intended to provide safe, controlled fluid removal in patients with fluid overload for up to 8 to 24 hours. These patients all suffer from decompensated chronic CHF and are admitted or on the verge of admission to a hospital. Regardless of the exact nature of their disease theses patients present at the hospital with a number of symptoms that manifest fluid overload and result in difficulty of breathing and pulmonary edema require immediate treatment. These patients are typically 5 to 20 kg over their dry weight and, if treated with diuretics, can tolerate fluid removal rates of up to 0.5 L/hour for until symptoms are relieved.

The intended use of the present invention is to assist in the initial removal of 2 to 4 liters of fluid that should result in the relief of symptoms and much improved responsiveness to medication. The present invention can be performed by a physician or nurse trained in the use of the device. Treatment can be performed in the setting of a monitored hospital floor, outpatient clinic or Emergency Room. The present invention is prescribed by a cardiologist. The main idea behind the present invention is to remove excess water from the patient's blood using a well-accepted ultrafiltration technique at the same rate at which the surplus fluid can be recruited from the tissue.

The intended use of the present invention is slow continuous removal of fluid by ultrafiltration of blood. Excessive removal of fluid can lead to hypotension and serious risks to health. If the fluid is removed from vascular space too fast, it is equally dangerous and can lead to hypotension. The principle method of treatment with the present invention is to remove fluid at a rate that allows vascular blood volume to be replenished with water that has accumulated in the interstitial space as a result of the patient's condition. Patients that should be treated by the present invention are typically 10 to 20 kg over their dry weight due to this excess water.

Potential excessive water loss or gain is a recognized hazard associated with RRT. Modern CRRT machines used in SCUF or CVVH mode can potentially remove and replace tens of liters of fluid from patient in a space of several hours. As a result, even a small error in fluid balance can result in severe risks to a patient. To prevent this from happening accurate ultrafiltration controllers are used that are based on continuous measurement of the weight of extracted and infused fluids. Ultrafiltration rate is adjusted accordingly by controlling the speed of an ultrafiltration pump that can apply negative or positive pressure to the ultrafiltration side of the filter membrane.

In the case of the present invention, fluid gain is not a risk. The present invention is designed for fluid removal only. To prevent excessive removal of fluid from the patient, the present invention relies on a number of inherently safe features and materials properties rather than the ultrafiltrate pump controller.

Ultrafiltrate rate (UF) is a function of TMP, Permeability of the membrane and the membrane surface. Membrane surface is a constant and in the case of the present invention is 0.1 $m^2$. Permeability of a filter membrane, is expressed as ml of ultrafiltrate per hour per unit of the membrane surface area. Permeability of the present invention filter membrane is 30 to 33 mL/hour/$m^2$/mmHg. The resulting KUF of the filter is 3 mL/hr/mmHg. KUF of a filter can decrease during the operation owing to the fouling of the membrane but can not increase unless the membrane is broken. Equation 2 takes into account the affects of oncotic pressure on the ultrafiltration rate. The KUF of the membrane is determined using animal blood at standard conditions such as hematocrit of 27%, temperature of 37° C. and appropriate concentration of protein and electrolytes. Although these conditions do not perfectly reflect clinical conditions in all patients it is a useful engineering approximation.

$$UF=TMP\times(KUF\times Area) \quad \text{(Equation 2)}$$

In the present invention, TMP is a function of blood flow and the resistance of circuit elements downstream, including the filter. TPM can be calculated in real time by the microprocessor using equation 3 from the readings of pressure transducers.

$$TMP=(Pp-Pr)/2+Pr-Pg \quad \text{(Equation 3)}$$

Where Pp is the pump (pre filter) pressure, Pr is the return (post filter) pressure and Pg is a pressure generated by the weight of the column of ultrafiltrate. Given the unadjustable design of the ultrafiltrate circuit, Pg is a constant. For the 20 cm level difference between the filter and the level of fluid in the bag Pg is 17 mmHg.

Substitution of the calculated TMP into Equation 2 gives a reasonable estimate of the ultrafiltration rate.

During the use of the present invention the operator sets the maximum allowed rate of ultrafiltration in mL/hour. Values between 100 and 500 mL/hour are allowed. The present invention microprocessor establishes the rate of withdrawal of blood in the range of 40 to 60 mL/min. This flow rate is determined by the quality of access. It is advantageous to establish and maintain blood flow constant.

Based on the pressure sensor readings the TMP is calculated. This allows the calculation of ultrafiltrate rate for known KUF of the filter.

If the ultrafiltration rate is higher than desired it is reduced using a solenoid ultrafiltrate pinch valve attached to the filtrate line 211. When the valve is closed the pressure inside the ultrafiltrate compartment of the filter 6 rises rapidly until it is equal to the pressure in the blood compartment (fibers). When the system is in equilibrium, no ultrafiltration occurs. The pinch valve is cycled approximately once per minute. The duty cycle (ratio of open to closed state) is calculated ratiometrically from the actual and desired ultrafiltration rate.

Blood exiting the filter 207 through the connector on the bottom of the filter casing is continuously returned to the patient through the return needle 210. Blood flow leaving the filter is the same as the blood flow entering the filter if the ultrafiltrate clamp 213 is closed. If the clamp 213 is open ultrafiltration occurs and the blood is continuously fractured into the ultrafiltrate and more concentrated blood. The hematocrit and the volume of returned blood was determined by the ultrafiltration fraction, which is the volumetric fraction of the ultrafiltrate relative to the volume of whole blood entering the filter.

Blood return circuit pressure sensor 209 serves several functions. The return pressure is used in the TMP calculation that is in turn used to calculate input data for the control of the ultrafiltration rate. It is also used to detect a disconnected or occluded circuit. Excessive pressure signals the occlusion that can be caused by a kinked tube or a clotted needle. Since the resistance of the needle 210 is much higher than the resistance of the infusion blood line 224, disconnection of the needle from the tubing is easy to detect from an adapt drop of the return pressure.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An extracorporeal blood circuit comprising:

a withdrawal tube connectable at a first end to [a first peripheral blood vessel] *a vascular system* of a mammalian patient;

a filter having a blood input connectable to a second end of the withdrawal tube;

a return tube having a first end connectable to an output of the filter and a second end connectable to [a second peripheral blood vessel] *the vascular system*;

a continuous blood passage is formed in said withdrawal tube, filter and return tube through which blood is withdrawn from the [first peripheral blood vessel] *vascular system*, filtered and returned to the [second blood vessel;] *vascular system, and*

[wherein said continuous blood passage is air free and]

further wherein said filter has a concentration rise flow volume of no greater than 15% of the total volume of the filter, where the concentration flow volume is defined as a volume of flow through the output of the filter during which a concentration of a first fluid flowing through the filter output rises from a concentration of 10% to a concentration of 90%.

2. An extracorporeal blood circuit as in claim 1 wherein said circuit has a perfusion volume interval of less than 30 percent of a filling volume of the circuit for an increase of a concentration of an output flow of the circuit from 10% concentration to 90% concentration of an input flow.

3. The extracorporeal blood circuit as in claim 1 wherein a concentration of blood flow at an output of the circuit is 90% of an input concentration after perfusion through the filter, with less than 110 percent of a filling volume of the circuit following an increase of a concentration of flow into the withdrawal tube.

4. A method for moving blood through an extracorporeal blood circuit having a withdrawal tube connected to a [first blood vessel] *vascular system* of a mammalian patient, a filter and a return tube connected to [a second blood vessel] *the vascular system* and a pump acting on the circuit, wherein the method comprises:

withdrawing blood from the [first blood vessel] *vascular system* into the withdrawal tube;

moving blood through the circuit by action of the pump;

filtering the blood flowing through the filter from the withdrawal tube, wherein the blood enters an inlet to the filter and flows out of a blood output;

returning blood flowing from the blood output through the return tube to the [second blood vessel] *vascular system*, and wherein said filter has a concentration rise volume of no greater than 15% of a total blood volume in the filter, where the concentration rise volume is defined as a volume of flow from the output from the filter occurring after an abrupt change at the inlet to the filter from a first fluid to a second fluid and as a concentration of the second fluid flowing through the output rises from 10% of fluid flowing through the output to 90% of said fluid flowing through the output.

5. A method for moving blood through an extracorporeal blood circuit having a withdrawal tube connected to a [first blood vessel] *vascular system* of a mammalian patient, a filter and a return tube connected to [a second blood vessel] *vascular system* and a pump acting on the circuit, wherein the method comprises:

withdrawing blood from the [first blood vessel] *vascular system* into the withdrawal tube; moving blood through the circuit by action of the pump;

filtering the blood flowing from the withdrawal tube and into the filter, returning blood output from the filter through the return tube to the [second blood vessel] *vascular system*, and after abruptly switching an input flow to the filter from a first fluid to a second fluid, measuring the output flow from the filter to be no greater than 15% of a total blood path volume of the filter as a concentration of the second fluid at the outlet of the filter raises from a 10% concentration level to a 90% concentration level.

6. A method for moving blood through an extracorporeal blood circuit having a withdrawal tube connected to a [first blood vessel] *vascular system* of a mammalian patient, a filter and a return tube connected to [a second blood vessel] *the vascular system* and a pump acting on the circuit, wherein the method comprises:

withdrawing blood from the [first blood vessel] *vascular system* into the withdrawal tube; moving blood through the circuit by action of the pump;

filtering the blood flowing from the withdrawal tube and into an inlet of the filter, returning blood output through a filter output from the filter through the return tube to the [second blood vessel] *vascular system*, and abruptly switching an input flow to the inlet from a first fluid to a second fluid such that a transition fluid volume flowing from the blood outlet of the filter does not exceed 15% of a total volume of a blood path in the filter, where the transition fluid volume is a fluid having more that a concentration of at least 10% of the second fluid and less than 90% of the second fluid.

7. A method as in claim 6 wherein the second fluid is blood.

8. A method as in claim 6 wherein the first fluid is of a conductivity substantially different than a conductivity of the second fluid.

9. A method for moving blood through an extracorporeal blood circuit having a withdrawal tube connected to a [first blood vessel] *vascular system* of a mammalian patient, a filter and a return tube connected to [a second blood vessel] *vascular system* and a pump acting on the circuit, wherein the method comprises:

withdrawing blood from the [first blood vessel] *vascular system* into the withdrawal tube; moving blood through the circuit by action of the pump;

filtering the blood flowing from the withdrawal tube and into an inlet of the filter, wherein the filter has a blood path, and said blood path has a total volume of blood in the filter;

returning blood output through a blood output from the filter through the return tube to the [second blood vessel] *vascular system*, abruptly switching an input fluid to the inlet of the filter from a first fluid to a second fluid;

detecting a transition volume of mixed fluid flowing through the blood outlet, wherein said transition volume does not exceed 15% of the total volume of the blood path and wherein the transition volume is a fluid mixture having at least 10% and no more than 90% of the first fluid.

10. A method as in claim 9 wherein the second fluid is blood.

11. A method as in claim 9 wherein the first fluid is of a conductivity substantially different than a conductivity of the second fluid.

12. A method for moving blood through an extracorporeal blood circuit having a withdrawal tube connected to a [first blood vessel] *vascular system* of a mammalian patient, a filter and a return tube connected to a [second blood vessel] *vascular system* and a pump acting on the circuit, wherein the method comprises:

withdrawing blood from the [first blood vessel] *vascular system* into the withdrawal tube; moving blood through the circuit by action of the pump;

filtering the blood flowing from the withdrawal tube and into an inlet of the filter, wherein the filter has a blood path, and said blood path has a total volume of blood in the filter;

returning blood output through a blood output from the filter through the return tube to the [second blood vessel] *vascular system*, abruptly switching an input fluid to the inlet of the filter from a first fluid to a second fluid, and a transition flow period is no greater than a period during which 15% of the total volume of the blood path of the filter flows through the filter output, where the transition flow period starts when a fluid mixture at the filter output has at least 10% concentration of the second fluid and no more than 90% concentration of the first fluid.

13. A method as in claim 12 wherein the second fluid is blood.

14. A method as in claim 12 wherein the first fluid is of a conductivity substantially different than a conductivity of the second fluid.

* * * * *